(12) United States Patent
Wei et al.

(10) Patent No.: US 6,721,591 B2
(45) Date of Patent: Apr. 13, 2004

(54) METHOD OF DERIVING STANDARD 12-LEAD ELECTROCARDIOGRAM AND ELECTROCARDIOGRAM MONITORING APPARATUS

(75) Inventors: Daming Wei, Fukushima (JP); Takeshi Kojima, Tokyo (JP); Tadashi Nakayama, Tokyo (JP); Yoshio Sakai, Tokyo (JP)

(73) Assignees: Nihon Kohden Corporation, Tokyo (JP); Daming Wei of the University of Aizu Faculty House, Fukushima (JP)

( * ) Notice: Subject to any disclaimer, the term of this patent is extended or adjusted under 35 U.S.C. 154(b) by 196 days.

(21) Appl. No.: 09/910,837

(22) Filed: Jul. 24, 2001

(65) Prior Publication Data

US 2002/0045837 A1 Apr. 18, 2002

(30) Foreign Application Priority Data

Jul. 24, 2000 (JP) ................................. P. 2000-221741

(51) Int. Cl.[7] ............................................. A61B 5/0402
(52) U.S. Cl. ........................................ 600/509; 600/512
(58) Field of Search ............................... 600/509, 512; 128/920

(56) References Cited

U.S. PATENT DOCUMENTS

| | | | |
|---|---|---|---|
| 4,850,370 A | 7/1989 | Dower | 128/699 |
| 5,058,598 A | 10/1991 | Nicklas et al. | |
| 5,231,990 A * | 8/1993 | Gauglitz | 600/510 |
| 5,711,304 A | 1/1998 | Dower | 128/696 |
| 6,025,615 A | 2/2000 | Liu et al. | |
| 6,119,035 A | 9/2000 | Wang | |

OTHER PUBLICATIONS

American Heart Journal (The Image Surface of a Homogeneous Torso).
Journal of Electrocardiology vol. 21 Supplemental Issue 1998.

* cited by examiner

Primary Examiner—Kennedy Schaetzle
(74) Attorney, Agent, or Firm—Sughrue Mion, PLLC

(57) ABSTRACT

A plurality of electrodes for measuring electrocardiogarphic waveforms are attached on body surface positions that constitute a subset of the standard 12-lead system. The measured electrocardiogarphic waveforms of said subset of said standard 12-lead system are used to calculate the electrocardiogarphic waveforms of remaining leads in the said standard 12-lead system. The measured and calculated electrocardiographic waveforms are synthesized to form a standard 12-lead electrocardiogram. The invention is capable of monitoring the 12-lead electrocardiogram with a reduced number of electrodes, wherein a portion of waveforms are directly measured and used as primary information for diagnosing heart disease, and the other portion of waveforms are derived from the measured leads and are used as a secondary information for improving the accuracy of diagnosis. The invention is especially useful in monitoring ischemic heart disease and acute myocardial infarction in cases where mounting and maintaining ten electrodes to obtain 12-lead electrocardiogram is difficult, such as in ambulatory monitoring, long-term monitoring and home monitoring.

6 Claims, 5 Drawing Sheets

METHOD OF DERIVING STANDARD 12-LEAD ELECTROCARDIOGRAM AND ELECTROCARDIOGRAM MONITORING APPARATUS

BACKGROUND OF THE INVENTION

1. Field of the Invention

The present invention relates to a method of deriving a standard 12-lead electrocardiogram for diagnosing heart disease including ischemic heart disease, acute myocardial infarction, and others by using a reduced number of electrodes attached to predetermined positions on the surface of a living body, and a electrocardiogram monitoring apparatus using the electrocardiogram derivation methods.

2. Related Art

To detect, measure, and record a conventional 12-lead electrocardiogram from a subject in a hospital or the like, a total of ten electrodes are attached to the surface of the subject's body; six positions on the chest and four positions at the limb. Heart potentials sensed by those ten electrodes are input to an apparatus, namely electrocardiograph. The electrocardiograph produces twelve waveforms; six waveforms of limb leads, named as I, II, III, aVR, aVL, aVF, and six waveforms of chest leads named as V1, V2, V3, V4, V5, and V6.

The 12-lead electrocardiogram is a standard in diagnosing heart disease. It is especially important for diagnosing ischemic heart disease and acute myocardial infarction, where waveform changes such as the T wave and the ST segment changes in all leads have to be examined at the same time. Because ten electrodes are required to record 12-lead electrocardiogram, the recording and/or monitoring are usually performed in an environment where the subject is kept quiet. In many practical situations, however, mounting and maintaining such ten electrodes to record the 12-lead electrocardiogram are almost impractical. One example is ambulatory monitoring. It is also very difficult to do this for long-term bedside monitoring, because the number of electrodes and configuration severely restrict the mobility of the patient. Technically, most monitors use telemetry and at least eight channels of signal are necessary to be transmitted for the 12-lead electrocardiogram. This is not only expensive in cost, but also sometimes impossible because of the restriction of capacity in telecommunication. For example, most current telemonitors used in an ambulance usually have only one channel to transmit the electrocardiogram, which may be sufficient for diagnosing arrhythmias, but insufficient for diagnosing ischemic heart disease and acute myocardial infarction that are main causes of heart death. To put it into a nutshell, the problem is that there is a necessity to record and monitor the 12-lead electrocardiogram, but there is no means to mount and maintain such ten electrodes in many practical circumstances such as ambulatory monitoring, long-term bedside monitoring, homecare monitoring and so on.

To meet the need of monitoring 12-lead ECG in cases where mounting and maintaining ten electrodes are difficult, there is proposed a means called EASI lead system and EASI electrocardiogram (U.S. Pat. No. 4,850,370, and G. E. Dower, "EASI-lead electrocardiography, Totemite Inc. Point Robeerts, Wash., 1996). The EASI lead system includes five electrodes: electrode E on the lower sternum, electrode A on the left axilla, electrode S on the upper sternum, electrode I on the right axilla, and an additional grounding electrode. The potential differences of A-I, E-S and A-S are recorded and the 12-lead electrocardiogram is calculated with coefficients developed by the inventor.

However, there are some difficulties for the electrocardiogram to be widely accepted by the clinical practice. An inherent limitation is due to the fact that all the 12-lead waveforms of the EASI electrocardiogram are calculated ones, not directly recorded ones. That means the EASI electrocardiogram only provides indirect, or secondary information. In clinical practice, most physicians generally do not trust secondary information for diagnosis. In addition, relevant laws in most counties prohibit using such estimated information for diagnostic behavior. Furthermore, most medical persons are not familiar with the EASI electrocardiogram. In any event, it is a fact that the EASI electrocardiogram is not easily accepted in clinical practice.

With ten electrodes placed in positions as shown in FIG. 1 and FIG. 2, the 12-lead electrocardiogram is defined as follows.

TABLE 1

| | |
|---|---|
| I: | $vL - vR$ |
| II: | $vF - vR$ |
| III: | $vF - vL$ |
| aVR: | $vR - (vL + vF)/2$ |
| aVL: | $vL - (vR + vF)/2$ |
| aVF: | $vF - (vL + vR)/2$ |
| V1: | $v1 - (vR + vL + vF)/3$ |
| V2: | $v2 - (vR + vL + vF)/3$ |
| V3: | $v3 - (vR + vL + vF)/3$ |
| V4: | $v4 - (vR + vL + vF)/3$ |
| V5: | $v5 - (vR + vL + vF)/3$ |
| V6: | $v6 - (vR + vL + vF)/3$ |

SUMMARY OF INVENTION

Accordingly, an objective of the present invention is to provide a method of deriving a standard 12-lead electrocardiogram and a 12-lead electrocardiogram monitoring apparatus in which the 12-lead electrocardiogram measurement uses a reduced number of electrodes for sensing the body surface potentials on positions of a subset of the standard 12-lead system, so that a portion of the resultant 12-lead waveforms are obtained directly from measured signals, as the direct or primary information for diagnosis, and others are derived from the measured signals, as the secondary and auxiliary information for improving the accuracy of diagnosis.

According to an aspect of the present invention, there is provided a method of deriving a standard 12-lead electrocardiogram comprising the steps of: attaching a plurality of electrodes on positions of a subset of the standard 12-lead system used in routing rest 12-lead electrocardiogram testing, or a subset of another standard lead system, called M-L lead system, used in routing exercise 12-lead electrocardiogram testing; sensing and measuring the body surface potentials from the plurality of electrodes; calculating waveforms of unmeasured leads of the standard 12-lead lead systems; and constructing the 12-lead electrocardiogram in which a portion of waveforms are obtained from directly measured signals and the other portion of waveforms are derived by the calculation.

In the method of deriving a standard 12-lead electrocardiogram, an array, called heart vector, is obtained, as an intermediate quantity, based on measured signals of leads and the values of lead vectors of the measured leads, which are available according to publications of Frank (E. Frank, "The image surface of a homogeneous torso," Am Heart J, 47: 757–768, 1954). The heart vector is calculated for each time instant of sampling. The waveforms of unmeasured leads in the standard 12-lead system are derived using the heart vector together with values of lead vectors of the unmeasured leads, which are also available according to publications of Frank as mentioned.

In the method of deriving a standard 12-lead electrocardiogram, the said plurality of electrodes can include RA, LA, RL, LL, V1, and V6 of the standard 12-lead system (FIG. 1) used in said routing rest 12-lead electrocardiogram testing, or of said M-L lead system (FIG. 2) used in routing exercise testing; the said plurality of electrodes can also include RA, LA, RL, LL, V1, and V5 of the standard lead system used in said routing rest 12-lead electrocardiogram testing, or of said M-L lead system used in routing exercise testing;

In the method of deriving a standard 12-lead electrocardiogram, the waveforms of limb leads and measured chest leads are obtained according to Table 1. The remaining unmeasured chest leads are derived based on said method.

According to another aspect of the invention, there is provided an electrocardiogram monitoring apparatus using the method of deriving a standard 12-lead electrocardiogram of the present invention, comprising; a plurality of electrodes attached to the surface of a living body, for sensing and measuring electrocardiographic potentials on positions of a subset of the standard 12-lead system; a potential detector for detecting the potentials from said electrodes; an operational amplifier for amplifying the potential signals and obtaining waveforms of leads from said potentials detector; a 12-lead electrocardiogram operation unit for synthesizing and calculating waveforms of undetected leads of the standard 12-lead system using data of waveforms of said obtained leads from the amplifier; and a 12-lead electrocardiogram display unit for displaying 12-lead electrocardiogram waveforms received from said 12-lead electrocardiogram operation unit.

BRIEF DESCRIPTION OF DRAWINGS

FIGS. 4 and 5 are used here for a comparison between the measured and derived waveforms.

DETAILED DESCRIPTION OF PREFERRED EMBODIMENT

Principle of Present Invention

Figure 1:
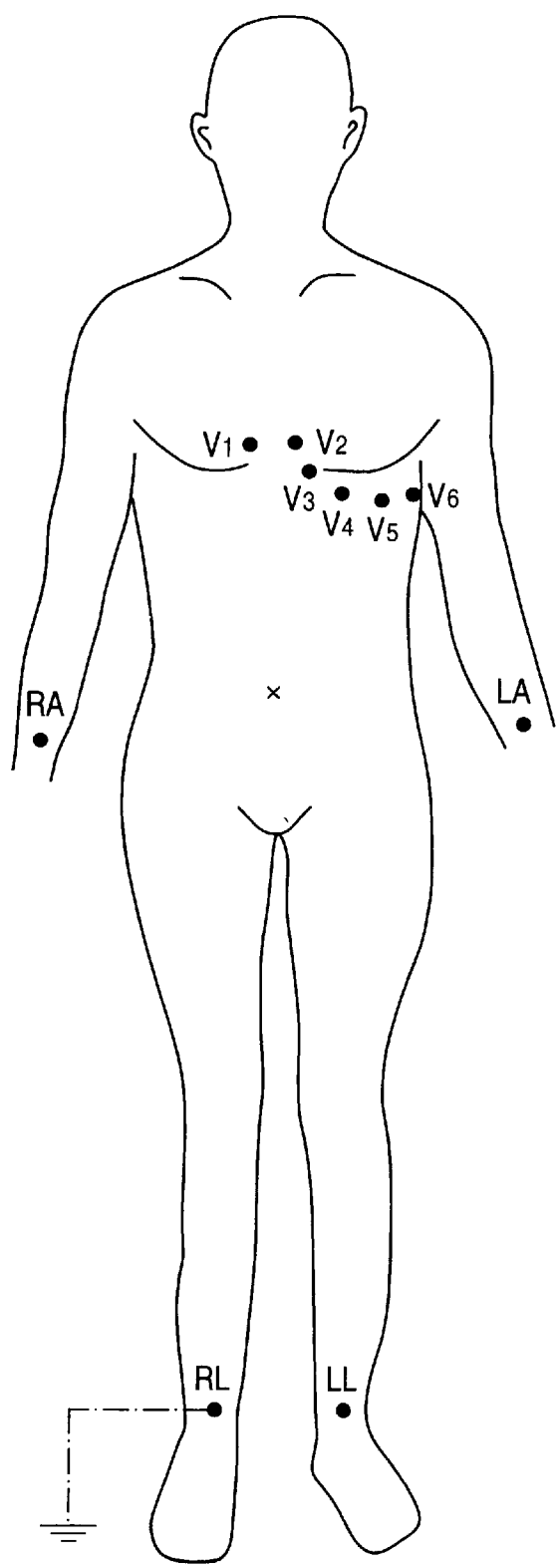
FIG. 1 is a diagram explaining the electrode positions of a standard lead system used in routing rest 12-lead electrocardiogram testing, from which a subset of electrode positions can be used in sensing the body surface potentials as an embodiment of the present invention.

The principle of the present invention is based on the fact that there is information redundancy in the standard 12-lead electrocardiogram. In most electrocardiogram machines, signals of eight leads (I, II, V1 through V6) are recorded. These signals are not completely independent. According to the fixed dipole model of the heart, which interprets the electrocardiogram in a good precision, there are only three independent variables, so that it is possible to record electrocardiogram signals with a portion of the standard leads and to derive electrocardiogram for other leads. In this way, the 12-lead electrocardiogram provides raw signals with the recording leads as primary information and provides secondary information with derived leads as reference in improving accuracy of diagnosis.

Specifically, the subset of the lead system using a least number of channels includes the leads I and II of the limb leads for the standard 12-lead electrocardiogram or the ML leads, and the leads V1 and V5 or V6 of the chest leads. The lead III and the lead aV (aVR, aVL, aVF) are calculated on the basis of the characteristic relationship among the leads in table 1. The remaining chest leads V2, V3, V4 and V6 or V5 are calculated on the relationship among the potential matrix, the lead vector and the heart vector.

The electrodes for detecting the leads I and II are located at the left and right arms (LA, RA), and the left and right legs (LL, RL) for the limb leads. For the ML leads, the electrodes are located at four positions; positions (LA, RA) under the left and right clavicles and at the lower ends of the left and right anterior iliac spines or the lower ends (LL, RL) of the left and right costal arches. In this case, the RL is used as a grounding electrode. The electrodes for detecting the waveforms of leads of the two chest leads V1, and V6 or V5 are located at two positions; a right position of sternum in the $4^{th}$ rib interspace (V1) and a position (V6) on the left mid-axially line in the level on the left clavicle mid line in the $5^{th}$ rib interspace or a position (V5) on the left front-axially line in the level on the left clavicle mid line in the $5^{th}$ rib interspace. The subset of the lead system for the standard 12-lead electrocardiogram are detected and measured by using the electrodes thus attached. The remaining leads of the standard 12-lead electrocardiogram may be calculated on the basis of the characteristic relationship among the leads shown in Table 1.

Positions of a subset of the standard 12-lead system as used in the present invention are well known to educated medical people. Thus no additional training is necessary for using the method of present invention. This also ensures high accuracy in electrode placement and hence the diagnosis itself.

A method of deriving a standard 12-lead electrocardiogram and an electrocardiogram monitoring apparatus, which are believed as preferred embodiments of the present invention, will be described in detail with reference to the accompanying drawings.

DETAILED DESCRIPTION OF PRINCIPLES OF THE INVENTION

According to the fixed dipole model of the heart, the potential on a surface point can be described by:

$$v = L^T \cdot H \tag{1}$$

where L and H are column vectors with 3 elements, called lead vector and heart vector, respectively, denoted as:

$$H = \begin{bmatrix} h_x \\ h_y \\ h_z \end{bmatrix} \quad (2)$$

$$L = \begin{bmatrix} l_x \\ l_y \\ l_z \end{bmatrix} \quad (3)$$

and the superscript T represents matrix transposition.

The heart vector is the equivalent dipole source of the heart, which varies with time. The lead vector remains constant for a human subject, because the volume conductor of the torso is considered passive. Typical data of the lead vector for human was measured by Frank with a typical human torso model, called image surface (E. Frank, "The image surface of a homogeneous torso," Am Heart J, 47: 757–768, 1954). The data are used in the embodiment of the present invention.

If, for example, electrocardiographic signals of leads I, II, V1, and V6 are measured, the following equation can be established:

$$\begin{bmatrix} L_I^T \\ L_{II}^T \\ L_1^T \\ L_6^T \end{bmatrix} \begin{bmatrix} h_x \\ h_y \\ h_z \end{bmatrix} = \begin{bmatrix} V_I \\ V_{II} \\ V_1 \\ V_6 \end{bmatrix} \quad (4)$$

or $$L_{meas} H = V_{meas}$$

where the subscript "meas" represents measured leads.

Where L denotes values of lead vector components and V, the value of potential. Subscripts I, II, 1, and 6 stand for leads I, II, V1 and V6. T denotes the transposition operation. The least squares solution of equation (4) for H is equation (5).

$$H = (L_{meas}^T L_{meas})^{-1} L_{meas}^T V_{meas} \quad (5)$$

When the heart vector, H, is solved, values of potential of unmeasured leads, V2, V3, V4, and V5, are derived using formula (6):

$$\begin{bmatrix} V_2 \\ V_3 \\ V_4 \\ V_5 \end{bmatrix} = \begin{bmatrix} L_2^T \\ L_3^T \\ L_4^T \\ L_5^T \end{bmatrix} \begin{bmatrix} h_x \\ h_y \\ h_z \end{bmatrix} \quad (6)$$

where V, L and subscriptions are the same as described for equation (4).

Method of Deriving a Standard 12-lead Electrocardiogram

A method of deriving a standard 12-lead electrocardiogram according to the principle of the invention will be described.

FIG. 1 shows the electrode positions of a standard lead system from which a subset of positions are used in an embodiment of the invention when the measurement is based on the standard routing rest 12-lead electrocardiogram testing.

Figure 2:
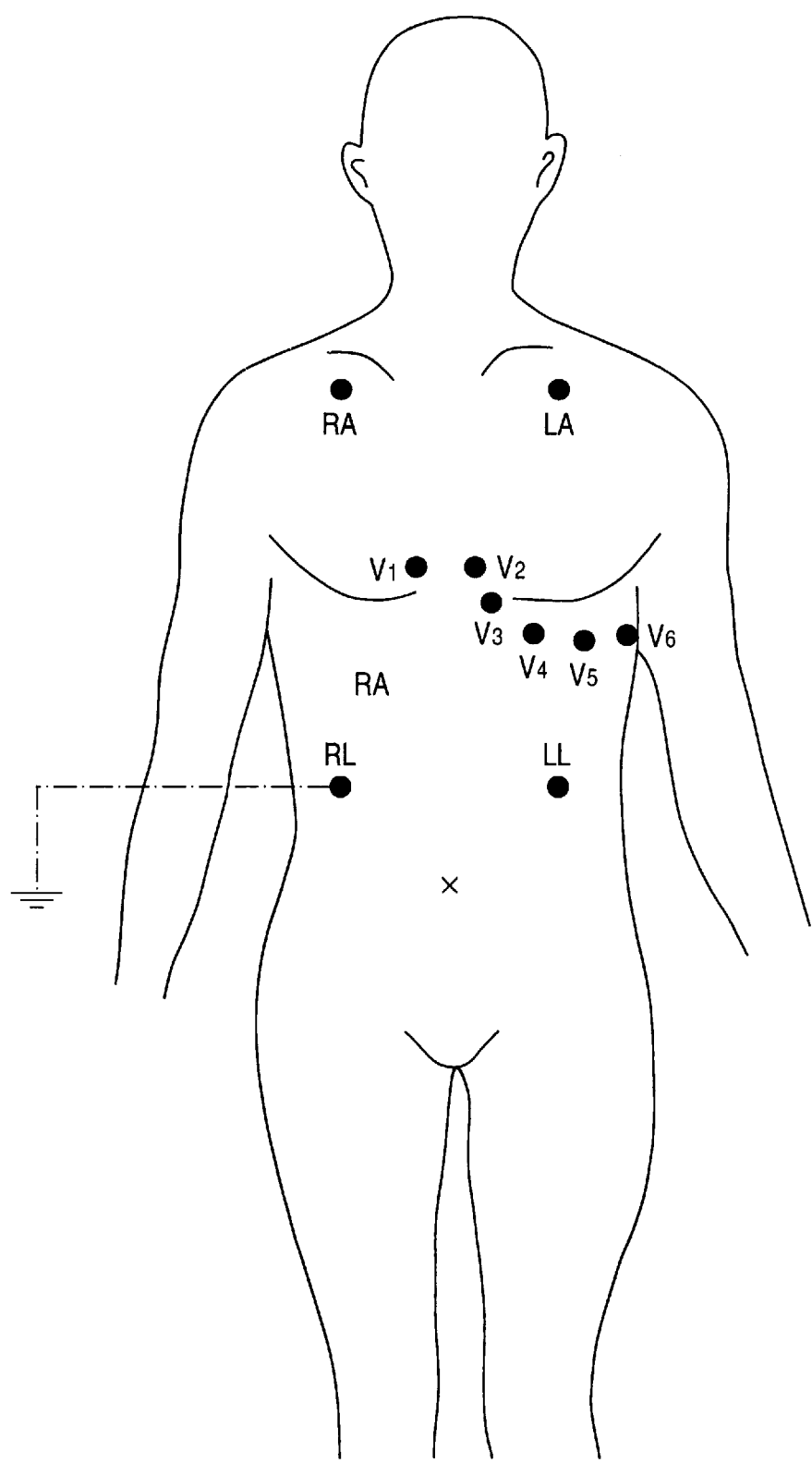
FIG. 2 is a diagram explaining the electrode positions of a standard lead system, called M-L lead system, used in routing exercise 12-lead electrocardiogram testing, from which a subset of electrode positions can also be used in sensing the body surface potentials as an embodiment of the present invention.

FIG. 2 shows the electrode positions of a standard lead system from which a subset of positions are used in an embodiment of the invention when the measurement is based on the routing exercise 12-lead electrocardiogram testing.

In an embodiment of the invention, positions of RA, LA, RL, LL, V1, and V6 are used. In another embodiment of the invention, positions of RA, LA, RL, LL, V1, and V5 are used.

The positions of electrodes shown in FIG. 1 and FIG. 2 are described as follows. In the figure, RA is a position of the right arm; LA is a position of the left arm; RL is a position of the right leg; and LL is a position of the left leg. Those positions shown in FIG. 2 are used when the standard 12-lead electrocardiogram is formed on the basis of the ML leads. In the figure, RA is a position under the right clavicle; LA is a position under the left clavicle; RL is a position of the lower end of the right anterior iliac spine or the right coastal arch; and LL is a position of the lower end of the left anterior iliac spine or the left coastal arch. In both FIGS. 1 and 2, V1 is a position of the right sternum in the fourth rib interspace; V6 is a position on the left mid-axillary line in the level of the line of the left mid-clavicular line the fifth rib interspace; V5 is a position on left front-axillary line in the level of the line of the left mid-clavicular line in the fifth rib interface. In those figures, the RL is a position at which a grounding electrode is placed.

If signals of four leads I, II, V1, and V6 are measured using electrodes described above, then using measured potentials of these leads, the heart vector (2) are calculated as an intermediate quantity by (5). Then the potentials of remaining chest leads, namely, V2, V3, V4, V5 are derived by (6).

The same can be done by exchange subscripts 6 and 5 in (4) and (6), if signals of four leads I, II, V1, and V5 are measured and waveforms of V2, V3, V4, V6 are to be derived.

Figure 3:
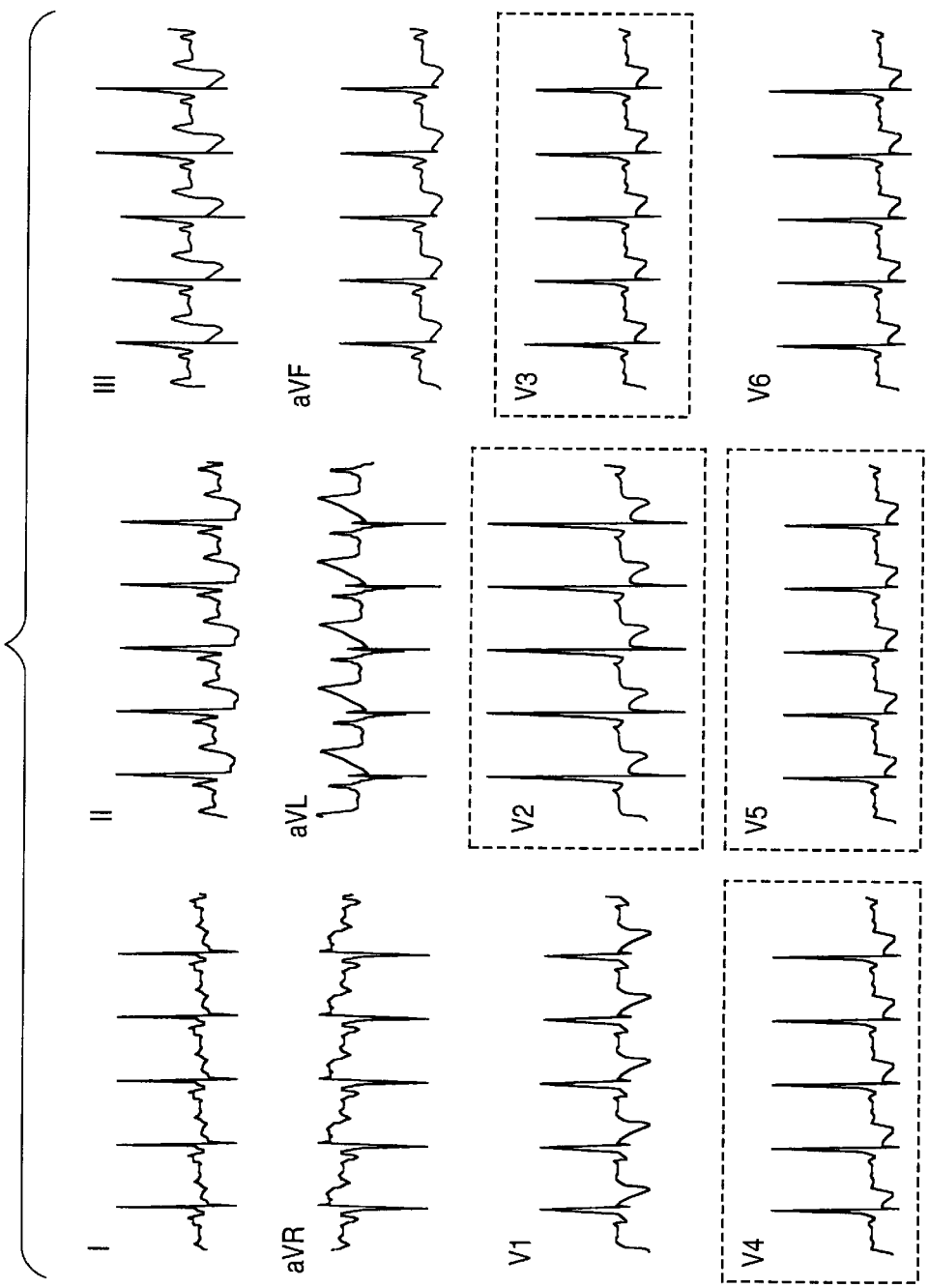
FIG. 3 shows waveforms of 12-lead electrocardiogram measured using M-L lead system.
Figure 4:
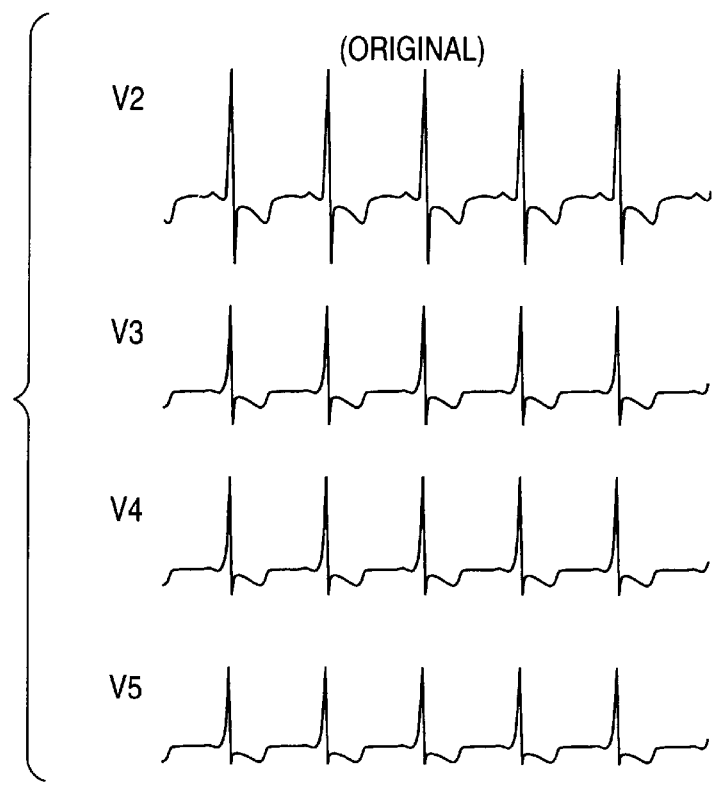
FIG. 4 shows the measured waveforms of V2, V3, V4, and V5 using M-L lead system.
Figure 5:
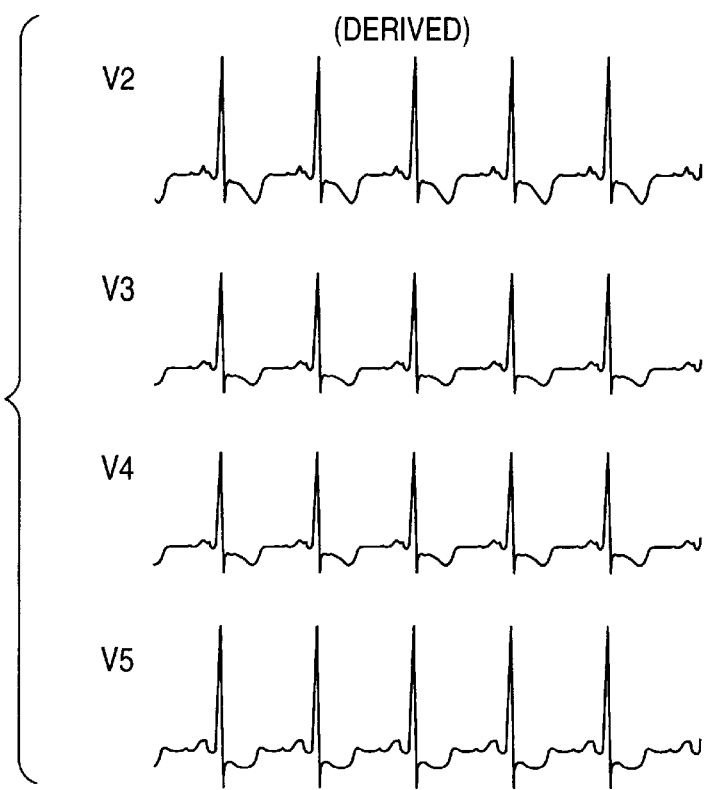
FIG. 5 shows the derived waveforms of V2, V3, V4, and V5 based on measured signals of leads I, II, V1, and V6.

A typical example showing the effectiveness of the present invention is shown in FIGS. 3, 4, and 5.

FIG. 3 shows raw waveforms of measured 12-lead electrocardiogram using M-L lead system. FIG. 4 displays the measured waveforms of V2, V3, V4, and V5 from FIG. 3 for comparison. FIG. 5 shows the derived waveforms of V2, V3, V4, and V5 based on measured signals of leads I, II, V1, and V6. A comparison between the measured and derived waveforms of these leads can be performed with FIGS. 4 and 5.

As observed from FIGS. 4 and 5, the accuracy of derivation is very satisfactory. For example, the main features of this case are the ST segment depression and T wave abnormality (inverse T in V2 and V3 and biphasic T in V4 and V5). These features are reconstructed in the derived ECG with good precision. It is clear that, added by the derived waveforms in V2 through V5, the accuracy of diagnosis would become higher than it would be if only the waveforms of measured leads (limb leads and V1 and V6) are used in diagnosis.

Figure 6:
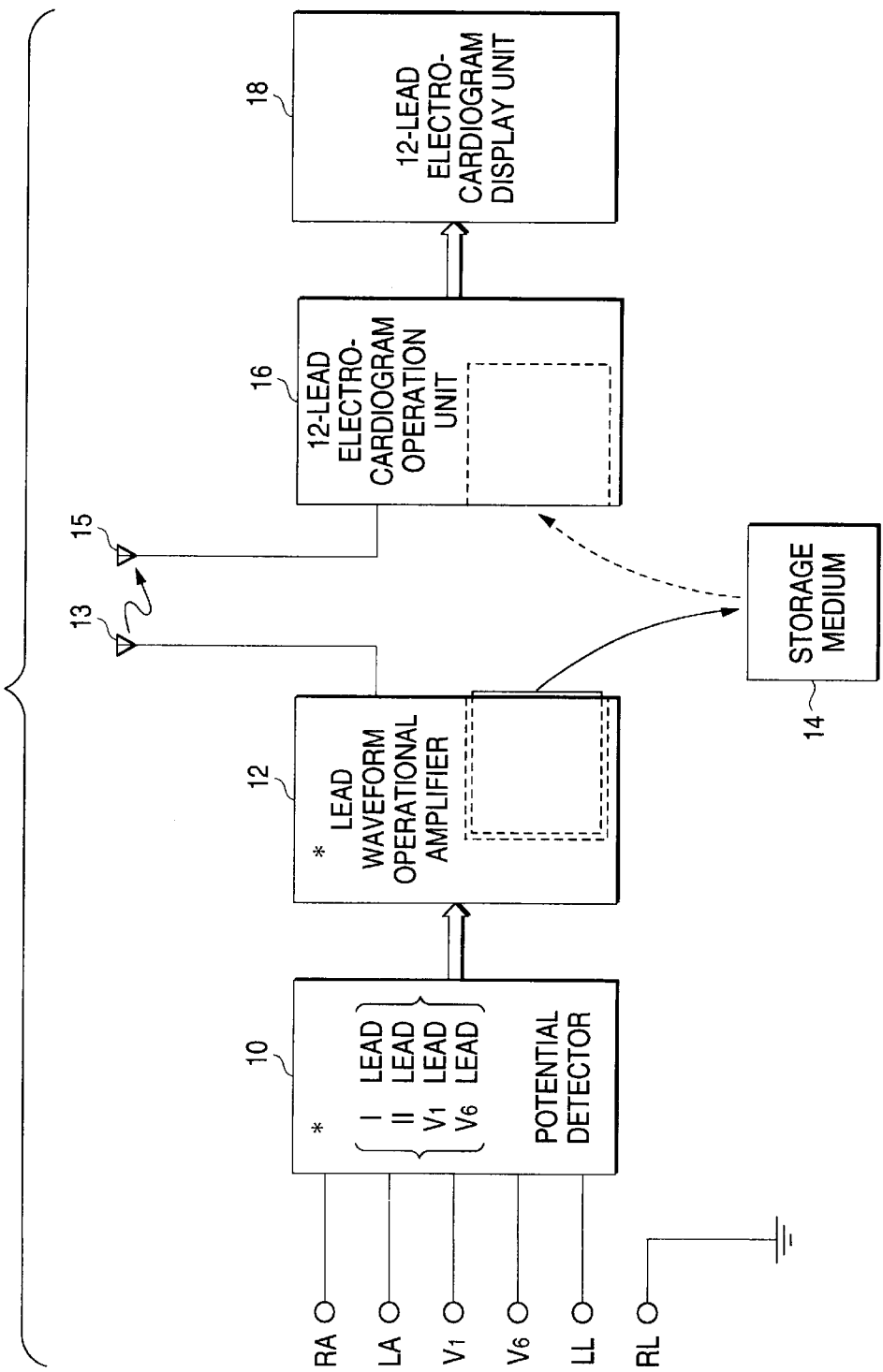
FIG. 6 is a system block diagram showing an electrocardiogram monitoring apparatus derived according to the present invention.

FIG. 6 shows a system configuration of an electrocardiogram monitoring apparatus that uses the method of deriving a 12-lead electrocardiogram described above. In FIG. 6, the reference numeral 10 designates a potential detector that senses potentials on electrodes RA, LA, RL, LL, V1 and V6, a subset of the standard 12-lead system shown in FIG. 1 or FIG. 2. Through 10, signals of lead I, II, V1, and V6 are input to the apparatus based on the relationship in Table 1, and amplified by an operational amplifier as designated as the reference numeral 12 in FIG. 6.

The amplified signals in 12 are then transmitted through an antenna 13 by a wireless transmitting means (not shown) and received through antenna 15 by a wireless receiving means (not shown) to an 12-lead electrocardiogram operation unit 16. Upon occasion, the amplified signals in 12 can be sent to 16 without using wireless transmitting/receiving means. In that case, the amplified signals in 12 are stored in a storage medium 14 and read out in 16 by replaying 14 in 16.

The 12-lead electrocardiogram operation unit 16 calculates waveforms of all limb leads based on relationship in Table 1, and unmeasured chest leads of the standard 12-lead system (in FIG. 6, they are waveforms of leads V2 through V5) based on formulas (5) and (6). The output of 12-lead electrocardiogram operation unit 16 is applied to a 12-lead electrocardiogram display unit 18 for monitoring. If required, the measured waveforms and the derived waveforms may be displayed in a way that enables easy visual discrimination between measured and derived waveforms. In FIG. 6, the input of potentials is from electrodes RA, LA, RL, LL, V1 and V6. However, the present invention is not limited to these applications. There can be many options to select the input leads from the standard 12-lead system as shown in FIGS. 1 and 2. Another example of an application using the present invention uses electrodes of RA, LA, RL, LL, V1 and V5. In that case, the waveforms of chest leads V2, V3, V4, V6 are derived from signals of I, II, V1 and V5.

Accordingly, the 12-lead electrocardiogram thus arranged is capable of properly and effectively monitoring a standard 12-lead electrocardiogram. The method and apparatus are especially useful in situations when mounting and maintaining 10 electrodes is difficult such as in ambulatory monitoring, long-term bedside monitoring, homecare monitoring, exercise monitoring, and others.

Having described a specific embodiment of our bearing, it should be understood that the invention is not limited to the described one, but may variously be modified, altered and changed without departing from the spirit and the scope of the invention.

One concerned example relative to the aforementioned description is the application of the invention to solve the problem of electrode detachment. This is a case that often happens when measuring the 12-lead electrocardiogram. In such case, if some electrodes are detached from the body surface, an electrode-detaching detector will easily detect the detaching. Then the potentials on the detached electrode can be reconstruction using measured signals based on the relationship of heart vector and lead vector as described in the above. The reconstructed waveforms can be displayed on the monitor screen or printed in the paper for reference in diagnosis. It is usually a good idea to display or print the reconstructed waveforms with different colors than that of measured waveforms to make easy discrimination.

As seen from the foregoing description, according to the present invention, there is provided a method of deriving a standard 12-lead electrocardiogram comprising the steps of: attaching a plurality of electrodes that constitute a subset of the standard 12-lead system for sensing and measuring potentials, measuring potential signals from the said electrodes; calculating waveforms of the remaining unmeasured leads in the standard 12-lead system using data taken from the measured leads; constructing the standard 12-lead electrocardiogram using measured and derived data of electrocardiogram.

One implementation of the invention as described above uses six electrodes on positions of RA, LA, RL, LL, V1, and V6, which constitute a subset of the standard 12-lead system as shown in FIG. 2. The electrode configuration is convenient for ambulatory and long-term monitoring. Furthermore, the electrode positions are found in every standard textbook of electrocardiogram and therefore well known to most medical professionals. As a result, it ensure good precise in electrode positioning, therefore ensure the good accuracy in measurement and derived waveforms.

As compared to other inventions such as EASI lead system and EASI electrocardiogram (U.S. Pat. No. 4,850, 370, and G. E. Dower, "EASI-lead electrocardiography, Totemite Inc. Point Robeerts, WA, 1996), the most important advantage of the present invention is that, in the resultant 12-lead electrocardiogram, the said method keeps original waveforms of eight leads as the direct and primary information, and provides remaining four derived waveforms as the secondary information to improve the accuracy of diagnosis. This feature is a very important advantage as compared to the EASI electrocardiogram, where all waveforms are derived from measured signals and therefore, only secondary information is available.

In addition to arrhythmias, ischemic heart disease and acute myocardial infarction are main cases that need continuous monitoring. For correct diagnosis of ischemic heart disease and acute myocardial infarction, the standard 12-lead electrocardiogram is necessary to be monitored in order to provide information of ST segment changes and other electrocardiogram features. Unfortunately, the conventional 12-lead system is impractical in cases of ambulatory monitoring, long-term bedside monitoring, homecare monitoring and others. The present invention provides a way to realize continuous 12-lead electrocardiogram monitoring. Therefore, the present invention is a great innovation in improving diagnosis of ischemic heart disease, acute myocardial infarction and other, and therefore is an important technique in saving human life.

What is claimed is:

1. A method of deriving a standard 12-lead electrocardiogram comprising the steps of:

attaching a plurality of electrodes for sensing and measuring body surface potentials on positions that constitute a subset of a standard 12-lead system;

measuring electrocardiographic waveforms for said subset from potentials sensed by said plurality of electrodes;

calculating waveforms of remaining leads of said standard 12-lead system from said measured electrocardiographic waveforms; and deriving the standard 12-lead electrocardiogram based on said measured electrocardiographic waveforms and said calculated electrocardiographic waveforms, wherein a heart vector is obtained from said measured waveforms based on an inherent relationship among said heart vector, lead vectors of said subset, and said measured electrocardiographic waveforms, and wherein said electrocardiographic waveforms of said remaining leads are calculated based on said heart vector and lead vectors of said remaining leads.

2. The method of deriving a standard 12-lead electrocardiogram according to claim 1, wherein said standard 12-lead electrocardiogram is a standard resting 12-lead electrocardiogram.

3. The method of deriving a standard 12-lead electrocardiogram according to claim 1, wherein said standard 12-lead electrocardiogram is a standard exercise 12-lead electrocardiogram.

4. The method of deriving the standard 12-lead electrocardiogram according to claim 1, wherein said electrodes are arranged at positions of RA, LA, RL and LL used in either a standard resting electrocardiogram testing or a standard exercise 12-lead electrocardiogram testing, and positions V1 and V6 in said standard 12-lead system, so that electrocardiographic waveforms of leads I, II, V1, and V6 are measured, and thereafter electrocardiographic waveforms of leads III, aVR, aVL, and aVF are derived based on a relationship among limb leads, and electrocardiographic waveforms of leads V2, V3, V4, V5 are derived based on said electrocardiographic waveforms of leads I, II, V1, and V6 with said step of deriving said standard 12-lead electrocardiogram.

5. The method of deriving the standard 12-lead electrocardiogram according to claim 1, wherein said electrodes are arranged at positions of RA, LA, RL and LL used in either a standard resting electrocardiogram testing or a standard exercise 12-lead electrocardiogram testing, and positions V1 and V5 in said standard 12-lead system, so that electrocardiographic waveforms of leads I, II, V1, and V5 are measured, and thereafter the electrocardigraphic waveforms of leads III, aVR, aVL, and aVF are derived based on a relationship among limb leads, and electrocardiographic waveforms of leads V2, V3, V4, V6 are derived based on said electrocardiographic waveforms of leads I, II, V1, and V5 with said step of deriving said standard 12-lead electrocardiogram.

6. An electrocardiogram monitoring apparatus comprising:

a plurality of electrodes, adapted to be attached to a surface of a living body, for sensing and measuring body surface potentials on positions that constitute a subset of a standard 12-lead system;

a potential detector for detecting potentials sensed by said plurality of electrodes;

an operational amplifier for detecting and amplifying potentials output from said potential detector;

a 12-lead electrocardiogram operation unit for calculating electrocardiographic waveforms of remaining leads of said standard 12-lead system based on signals from said operational amplifier and for deriving 12-lead electrocardiographic waveforms for display;

a 12-lead electrocardiogram display unit for displaying said 12-lead electrocardiographic waveforms, wherein the 12-lead electrocardiogram operation unit obtains a heart vector from values of said measured waveforms based on an inherent relationship among said heart vector, lead vectors of said subset, and said measured electrocardiographic waveforms, and wherein the 12-lead electrocardiogram operation unit calculates said electrocardiographic waveforms of said remaining leads based on said heart vector and lead vectors of said remaining leads.

* * * * *

UNITED STATES PATENT AND TRADEMARK OFFICE
CERTIFICATE OF CORRECTION

PATENT NO. : 6,721,591 B2
APPLICATION NO. : 09/910837
DATED : April 13, 2004
INVENTOR(S) : Daming Wei et al.

It is certified that error appears in the above-identified patent and that said Letters Patent is hereby corrected as shown below:

Title Page Under Item [73] Assignee, delete "Nihon Kohden Corporation (Tokyo, JP); Daming We the University of Aizu Faculty House (Fukushima, JP)" and insert -- Nihon Kohden Corporation (Tokyo, JP); Daming Wei (Fukushima, JP) --.

Signed and Sealed this

Twenty-eighth Day of November, 2006

JON W. DUDAS
*Director of the United States Patent and Trademark Office*